US012788731B2

(12) United States Patent
Golan et al.

(10) Patent No.: US 12,788,731 B2
(45) Date of Patent: Nov. 10, 2026

(54) USE OF 3-METHYLMETHCATHINONE

(71) Applicant: Ezekiel Golan, Vancouver (CA)

(72) Inventors: Ezekiel Golan, Vancouver (CA); Mark Haden, Vancouver (CA); Rene Van Wettum, Amsterdam (NL)

(73) Assignee: Ezekiel Golan, Vancouver (CA)

( * ) Notice: Subject to any disclaimer, the term of this patent is extended or adjusted under 35 U.S.C. 154(b) by 966 days.

(21) Appl. No.: 16/636,044

(22) PCT Filed: Aug. 2, 2018

(86) PCT No.: PCT/IB2018/055812
§ 371 (c)(1),
(2) Date: Feb. 3, 2020

(87) PCT Pub. No.: WO2019/026019
PCT Pub. Date: Feb. 7, 2019

(65) Prior Publication Data

US 2020/0360311 A1 Nov. 19, 2020

Related U.S. Application Data

(60) Provisional application No. 62/540,617, filed on Aug. 3, 2017.

(51) Int. Cl.

| | |
|---|---|
| ***A61K 31/38*** | (2006.01) |
| ***A61K 31/138*** | (2006.01) |
| ***A61P 25/00*** | (2006.01) |
| ***A61P 25/22*** | (2006.01) |

(52) U.S. Cl.
CPC ............ *A61K 31/138* (2013.01); *A61P 25/00* (2018.01); *A61P 25/22* (2018.01)

(58) Field of Classification Search
CPC ..... A61K 31/135; A61K 31/138; A61P 25/00; A61P 25/18; A61P 25/22; A61P 25/24; A61P 25/26
See application file for complete search history.

(56) References Cited

U.S. PATENT DOCUMENTS

| | | | | |
|---|---|---|---|---|
| 2010/0172916 A1 | 7/2010 | Gant et al. | | |
| 2011/0207718 A1 | 8/2011 | Bird | | |
| 2012/0108510 A1* | 5/2012 | Young | ..................... | A61P 25/30 514/10.7 |
| 2016/0000815 A1 | 1/2016 | Bird | | |
| 2016/0243197 A1 | 8/2016 | Goosens | | |

FOREIGN PATENT DOCUMENTS

| | | | |
|---|---|---|---|
| WO | WO 2010/015029 | 2/2010 | |
| WO | WO-2018195455 A1 * | 10/2018 | ............ A61K 45/06 |
| WO | WO 2019/026019 | 7/2019 | |

OTHER PUBLICATIONS

Adamowicz et. al., J. Analytical Tox., vol. 40, pp. 272-276, publ. Mar. 17, 2016 (Year: 2016).*
Motbey et. al., Addiction Biology, vol. 17, pp. 409-422, publ. 2011 (Year: 2011).*
International Preliminar Report on Patentability Dated Feb. 13, 2020 From the International Bureau of WIPO Re. Application No. PCT/IB2018/055812. (8 Pages).
International Search Report and the Written Opinion Dated Oct. 19, 2018 From the International Searching Authority Re. Application No. PCT/IB2018/055812. (15 Pages).
Al-Serori et al. "Investigations of the Genotoxic Properties of Two Synthetic Cathiones (3-MMC, 4-MMC) Which Are Used as Psychoactive Drugs", Toxicology Research, XP055511900, 5(5): 1310-1420, Published Online Jul. 22, 2016. p. 1410.
Amoroso et al. "Treating Posttraumatic Stress Disorder With MDMA-Assisted Psychotherapy: A Preliminary Meta-Analysis and Comparison to Prolonged Exposure Therapy", Journal of Psychopharmacology, 30(7): 595-600, Published Online Apr. 26, 2016.
Danforth et al. "MDMA-Assisted Therapy: A New Treatment Model for Social Anxiety in Autistic Adults", Progress in Neuro-Psychopharmacology & Biological Psychiatry, 64: 237-249, Available Online Mar. 25, 2015.
Krauss Whitburne "Psychotherapy Vs. Medications: The Verdict Is In: What Medications Can't Do for Your Mental Health, Psychotherapy Can", Psychology Today Website, 3 P., Jul. 21, 2015.
Luethi et al. "Pharmacological Profile of Mephedrone Analogs and Related New Psuchoactive Substances", Neuropharmacology, XP055512988, 134(Pt.A): 4-12, Available Online Jul. 26, 2017. p. 6.
Mithoefer et al. "The Safety and Efficacy of ±3,4-Methylenedioxymethamphetamine-Assisted Psychotherapy in Subjects With Chronic, Treatment-Resistant Posttraumatic Stress Disorder: The First Randomized Controlled Pilot Study", Journal of Psychopharmacology, 25(4): 439-452, Apr. 2011.

(Continued)

*Primary Examiner* — Sarah Pihonak

(57) ABSTRACT

The present invention relates to methods of drug-assisted psychotherapy with cathinone, particularly methods employing 3-methyl methcathinone (3-MMC). The present invention also relates to kits comprising 3-MMC for use in the treatment of subjects undergoing psychotherapeutic intervention. In particular, methods and kits for drug-assisted psychotherapy with 3-MMC for a variety of disorders and/or conditions, including PTSD, GAD and relationship distress are provided.

18 Claims, No Drawings

(56) References Cited

OTHER PUBLICATIONS

Sande "Characteristics of the Use of 3-MMC and Other New Psychoactive Drugs in Slovenia, and the Perceived Problems Experienced by Users", International Journal of Drug Policy, XP029387504, 27: 65-73, Published Online Apr. 1, 2015. p. 65.
Sessa et al. "Making A Medicine Out of MDMA", The British Journal of Psychiatry, 206(1): 4-6, Jan. 2015.
Shimshoni et al. "3-Methyl-Methcathinone: Pharmacokinetic Profile Evaluation in Pigs in Relation to Pharmacodynamics", Journal of Psychopharmacology, 29(6): 734-743, Published Online Mar. 24, 2015.

* cited by examiner

USE OF 3-METHYLMETHCATHINONE

FIELD AND BACKGROUND OF THE INVENTION

The present invention relates to methods of drug-assisted psychotherapy, particularly to methods employing 3-methyl methcathinone (3-MMC).

Traditional psychotherapy or counselling is relatively ineffective with the individuals most severely impacted by mental health issues or emotional health issues, and as a result, the current "best practice" alternative to traditional therapy or counselling is typically prescribing a wide range of psychiatric medications, which are often relatively ineffective and have unpleasant and even dangerous side effects.

Drug-assisted psychotherapy is a relatively new branch of psychiatry that brings together the benefits of drug and psychological treatments, with the goal of synergically enhancing each other's effects. One aspect of this interaction appear to be that the drug treatment enhances the patients rapport with the therapist, increases flexibility in the patient's mind, allowing the patient to discover and incorporate new ways of thinking about their situations/dilemmae. Furthermore, compliance with therapy is a long standing and difficult problem, potentially limiting the efficacy of all interventions and frequently being the most limiting factor in providing sustained psychotherapeutic benefit. Combining pharmacotherapeutic with psychotherapeutic intervention can improve compliance with treatment plans. Yet further, treatments that reduce anxiety help prevent episodes of dissociation and panic that can derail therapy.

There are ongoing, as well as completed clinical trials of MDMA-assisted psychotherapy (see, for example, NCT0009064; NTC02008396; NTC00353938; NTC01958593 and NCT01458327, NCT02427568), clinicaltrials(dot)gov/ct2/results?term=MDMA&Search=Search, exploring the uses of MDMA in clinical treatment of, inter alia, PTSD and anxiety.

Traditional psychostimulants such as amphetamine, cocaine or methylenedioxymethamphetamine (MDMA) all primarily target monoaminergic systems, leading to increased extracellular levels of serotonin (5-HT), dopamine (DA), and/or noradrenaline (NA). Experience with MDMA and cycloserine, as well as other psychoactive compounds has suggested benefit when used in psychotherapy, but has also revealed their shortcomings in the psychotherapeutic context. In general, amphetamines are associated with risk of amphetamine-psychosis, depression and cognitive impairment. In particular, serotonergic drugs such as MDMA, by stimulating an excess release of serotonin (and therefore possibly also triggering down-regulation of serotonin receptors in the brain), can create a rebound serotonin depletion and decreased sensitivity to the neurotransmitter following it's use, experienced by the user as depression and often lasting several days or more (for a review, see Danforth et al, Prog Neuro-Psych and Biol Psych, 2016, 64:237-249, or Amoroso et al, J. Psychopharm 2016, 30:595-600).

The cathinones are substituted amphetamines, differing in the character and location of the side residues around the central ring. All of 2-, 3- and 4-Methyl-methcathinone (2-, 3- and 4-MMC) are psychoactive drugs, producing increased alertness, wakefulness, euphoria and appetite suppression. Therapeutic use of 4-MMC as a psychostimulant has been proposed in US Patent Publications 20110207718; 20100172916 and 20160000815.

Additional publications relevant to drug assisted therapy with cathinones include, but are not limited to Mithoefer et al (J Psychopharmacol. 2011; 25: 439-452; J Psychopharmacol. 2013; 27: 28-39), Sessa et al (British J of Psychiatry 2015; 206:4-6), Shimshoni et al (J Psychopharmacol. 2015: 29:734-43) and Oehen et al (J Psychopharmacol. 2013; 27: 40-52).

SUMMARY OF THE INVENTION

According to an aspect of some embodiments of the present invention, there is provided a method for treating a subject undergoing a psychotherapeutic intervention comprising administering to the subject 3-methylmethcathinone (3-MMC).

According to an aspect of some embodiments of the present invention, the 3-MMC is administered prior to the psychotherapeutic intervention.

According to an aspect of some embodiments of the present invention, the 3-MMC is administered during the psychotherapeutic intervention.

According to an aspect of some embodiments of the present invention, the 3-MMC is administered at least twice during the psychotherapeutic intervention.

According to an aspect of some embodiments of the present invention, the 3-MMC is administered after the psychotherapeutic intervention.

According to an aspect of some embodiments of the present invention, the 3-MMC is administered to the subject in an amount of approximately 50 mg to approximately 500 mg per therapeutic intervention.

According to an aspect of some embodiments of the present invention, the 3-MMC is administered to the subject in an amount of approximately 100 mg to approximately 400 mg per therapeutic intervention.

According to an aspect of some embodiments of the present invention, the 3-MMC is administered to the subject in an amount of approximately 100 mg to approximately 200 mg per therapeutic intervention.

According to an aspect of some embodiments of the present invention, the 3-MMC is administered to the subject in an amount of approximately 100 mg or 200 mg per therapeutic intervention.

According to an aspect of some embodiments of the present invention, the psychotherapeutic intervention is for distress of the subject.

According to an aspect of some embodiments of the present invention, treating is for reducing the distress in the subject.

According to an aspect of some embodiments of the present invention, the distress is selected from the group consisting of cognitive, emotional, behavioral, relationship and spiritual distress.

According to an aspect of some embodiments of the present invention the distress is a condition or disorder selected from the group consisting of personal history of psychological trauma, parent-child relational problem, personal history (past history) of neglect in childhood, personal history (past history) of physical abuse in childhood, personal history (past history) of psychological abuse in childhood, personal history (past history) of sexual abuse in childhood, personal history (past history) of spouse or partner neglect, personal history (past history) of spouse or partner psychological abuse, personal history (past history) of spouse or partner physical violence, personal history (past history) of spouse or partner sexual violence, phase of life problem, relationship distress with spouse or intimate partner, stimulant use disorder and posttraumatic stress disorder.

According to an aspect of some embodiments of the present invention the subject is diagnosed with a stress-sensitive disorder selected from the group consisting of Post-traumatic Stress Disorder (PTSD), Bipolar Disorder, Acute Stress Disorder, anxiety disorders such as Generalized Anxiety Disorder, Obsessive-Compulsive Disorder, social anxiety disorders, Panic Disorders, phobias, obsessive compulsive disorders, and Trichotillomania.

According to an aspect of some embodiments of the present invention, the psychotherapeutic intervention is selected from the group consisting of psychoanalytic and psychodynamic therapy, behavioral therapy, cognitive therapy, humanistic therapy and integrative or holistic therapy.

According to an aspect of some embodiments of the present invention, the psychotherapeutic intervention is humanistic therapy or integrative/holistic therapy.

According to an aspect of some embodiments of the present invention, reducing the distress comprises at least one of the following: improving stability in the work/home environment, improving behaviors, improving employment functioning, improving vocational functioning, reducing cognitive stress, reducing emotional stress, improving the subject's living situation, improving the subject's family relationships, improving social relationships, improving the subject's sense of meaning to life, improving the subject's sense of purpose to life, reducing mental health symptoms, reducing addiction behaviors and reducing chemical dependencies.

According to an aspect of some embodiments of the present invention, reducing the distress comprises reducing the number and/or frequency of psychotherapeutic interventions, and/or reducing addiction behaviors and reducing chemical dependencies.

According to an aspect of some embodiments of the present invention there is provided a kit for use in treating a subject undergoing a psychotherapeutic intervention comprising a therapeutically effective amount of 3-methylmethcathinone (3-MMC) and instructions for the use of 3-MMC in conjunction with the psychotherapeutic intervention.

According to an aspect of some embodiments of the present invention, the psychotherapeutic intervention is for distress in the subject.

According to an aspect of some embodiments of the present invention, the psychotherapeutic intervention is selected from the group consisting of psychoanalytic and psychodynamic therapy, behavioral therapy, cognitive therapy, humanistic therapy and integrative or holistic therapy.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

DESCRIPTION OF SPECIFIC EMBODIMENTS OF THE INVENTION

The present invention relates to methods of drug-assisted psychotherapy with 3-methyl methcathinone (3-MMC). The present invention also relates to kits comprising 3-MMC for use in the treatment of subjects undergoing psychotherapeutic intervention.

Drug-assisted psychotherapy combines the psychostimulant properties of certain psychoactive drugs with a structured, psychotherapeutic environment in order to provide heightened insight, flexibility, trust and patient-therapist rapport. Clinical trials of drug-assisted psychotherapy with psychostimulants such as methylenedioxymethamphetamine (MDMA) have suggested beneficial effects when used in the psychotherapeutic context.

Some methyl methcathinones are potent psychostimulants. 4-methyl methcathinone (4-MMC, 4-methylephedrone, mephedrone) is known to have significant psychostimulant properties, but is considered unsuitable for drug-assisted psychotherapy, due to the pronounced anxiety and stress, and strong "redosing" effect characteristic of the later stages of 4-MMC stimulation. However, the present inventors have shown that 3-methyl methcathinone (3-MMC) provides significant enhancement of therapeutic efficacy when used in the psychotherapeutic context. Surprisingly, the present inventors have shown that, in certain cases, even a relatively limited regimen of 3-MMC-assisted psychotherapy sessions was sufficient to overcome significant obstacles to the patient's progress in therapy. Inter alia, the inventors have shown that 3-MMC-assisted psychotherapy can be effective in post-traumatic stress disorder (PTSD) therapy, couple's therapy and therapy for anxiety disorders.

Before explaining at least one embodiment of the invention in detail, it is to be understood that the invention is not necessarily limited in its application to the details set forth in the following description. The invention is capable of other embodiments or of being practiced or carried out in various ways.

One of the most important criteria in the success of psychotherapy or counselling is the connection between the therapist and the patient. The present inventors have found that 3-MMC can promote empathy and help to build a "therapeutic alliance" which can be an important predictor of a positive outcome for therapeutic or counselling process, encouraging deeper self-disclosure and greater follow-up in behavioural change commitments between sessions.

Further, 3-MMC is also effective in psychotherapy/counselling, possibly in part due to its ability to produce a sense of calming empowerment, allowing the individual to lower barriers preventing change and review, reframe, revise and even eliminate undesirable associations and memory patterns.

Still further, the present inventors have observed that 3-MMC is effective in the psychotherapeutic context in part due to its "portal effect", or deeply felt sense of accomplishment and transition, as well as 3-MMC's stimulation of creativity and relaxation of rigidity of thought patterns.

Thus, according to some embodiments, the present invention provides a method for treating a subject undergoing a psychotherapeutic intervention comprising administering to said subject 3-methylmethcathinone (3-MMC).

The term "treating" refers to inhibiting, preventing or arresting the development of a pathology (disease, disorder or condition) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology.

As used herein the phrase "psychotherapeutic intervention" refers to an intervention by a therapist employing methods of psychotherapy, with the intent of modifying an outcome. As used herein, the term "psychotherapy" refers to the use of psychological, as opposed to medical, methods, particularly when based on regular personal interaction with a therapist, with the goal of helping a person change and overcome problems in desired ways.

The realm of psychotherapeutic interventions includes a great variety of treatment modalities, ranging from traditional Freudian psychoanalysis to holistic therapies. Thus, according to some embodiments, psychotherapeutic interventions suitable for use with the methods of the invention include, but are not limited to psychoanalytic and psychodynamic therapy, behavioral therapy, cognitive therapy, humanistic therapy and integrative or holistic therapy.

Different categories of psychotherapeutic interventions can be distinguished from one another by their approach to well being. For example, as used herein, psychoanalytic therapy refers to a therapy based on Sigmund Freud's theories of the conscious and unconscious mind. Methods included within psychoanalytic therapy include, but are not limited to psychoanalysis, Freudian psychotherapy, abreaction therapy and transactional analysis.

As use herein, psychodynamic therapy refers to a type of psychology which has the primary focus of resolving unconscious conflicts in the human psyche. Interventions included within psychodynamic therapy include, but are not limited to Adlerian psychotherapy, Jungian psychotherapy, dreamwork therapy, intensive short-term dynamic psychotherapy, primal therapy and process oriented therapy.

As used herein, behavioral therapy refers to a type of therapy based on the belief that behaviors are learned and that unhealthy behaviors can be changed. Interventions included within behavioral therapy include, but are not limited to behavioural therapy, dialectical behavioural therapy, prolonged exposure therapy, flooding therapy, multimodal therapy, brief psychotherapy, functional analytic psychotherapy, reality therapy and systematic desensitization therapy.

As used herein, cognitive therapy refers to a type of therapy based on the belief that thinking patterns can be problematic and maladaptive thought processes can be changed. Interventions included within cognitive therapy include, but are not limited to, cognitive therapy, cognitive behavioural therapy, rational emotive behavioural therapy, emotional regulation therapy, stress reduction therapy, multimodal therapy, brief psychotherapy, rational living therapy and reality therapy.

As used herein, humanistic therapy refers to a type of therapy which looks at the whole person and believes that people are innately good and want to grow and self-actualize. Interventions included within humanistic therapy include, but are not limited to, humanistic therapy, gestalt therapy, client centred therapy, compassion focused therapy, existential therapy, emotionally focused therapy, emotional freedom technique therapy, motivational interviewing, Rogerian psychotherapy, attachment based psychotherapy, dyadic developmental psychotherapy, narrative therapy and positive psychology therapy.

As used herein, integrative or holistic therapy refers to a mixture of a variety of therapy techniques which includes all aspects of humanity and therefore is directed to an individual's overall physical, mental, spiritual, and emotional well-being. Interventions included within integrative or holistic therapy include, but are not limited to integrative therapy, holistic therapy, art therapy, expressive therapy, integrative body therapy, integral therapy, guided imagery therapy, visualization therapy, breathwork therapy, holotropic breathwork therapy, hypnotherapy, psychodrama therapy, eye movement desensitization and reprocessing therapy, sexual identity therapy, solution focused brief therapy, somatic therapy, somatic experiencing therapy, somatic psychology, systemic therapy, thought field analysis, mindfulness meditation therapy, addiction treatment therapy and transtheoretical model of change therapy.

It will be appreciated that any of the abovementioned psychotherapeutic interventions suitable for use with the methods of the invention can be employed individually with 3-MMC administration, as well as two or more types of psychotherapeutic interventions used in combination. In a non-limiting example, psychotherapeutic interventions suitable for use in the methods of the present invention can include cognitive-behavioral therapy combined with eye movement desensitization and reprocessing therapy (EMDR), or psychoanalysis combined with stress-reduction therapy.

Psychotherapeutic interventions particularly suited for use with the method of the invention include, but are not limited to interventions employing one or more of the following interventional elements: innovation rather than direction, non-directive compassion, encouraging subjects inner healing intelligence, paraphrasing, minimal encouragement, verbal and non-verbal, reflecting, emotional labeling, validating, allowing participants to arrive at their own conclusions, reassurance and waiting, unconditional positive regard, attunement and following not leading.

In some embodiments, a therapeutically effective amount of 3-MMC is administered to the subject. In some embodiments, 3-MMC is administered to the subject in an amount in the range of 5 mg per therapeutic intervention to 1000 mg per therapeutic intervention. In some embodiments, 3-MMC is administered to the subject in an amount in a range of approximately 7 mg to approximately 950 mg per therapeutic intervention, approximately 7 mg to approximately 950 mg per therapeutic intervention, approximately 10 mg to approximately 900 mg per therapeutic intervention, approximately 15 mg to approximately 850 mg per therapeutic intervention, approximately 20 mg to approximately 800 mg per therapeutic intervention, approximately 25 mg to approximately 780 mg per therapeutic intervention, approximately 30 mg to approximately 750 mg per therapeutic intervention, approximately 35 mg to approximately 700 mg per therapeutic intervention, approximately 40 mg to approximately 650 mg per therapeutic intervention, approximately 45 mg to approximately 600 mg per therapeutic intervention, approximately 50 mg to approximately 550 mg per therapeutic intervention, approximately 52 mg to approximately 500 mg per therapeutic intervention, approximately 57 mg to approximately 480 mg per therapeutic intervention, approximately 60 mg to approximately 450 mg per therapeutic intervention, approximately 63 mg to approximately 430 mg per therapeutic intervention, approximately 70 mg to approximately 400 mg per therapeutic intervention, approximately 75 mg to approximately 370 mg per therapeutic intervention, approximately 77 mg to approximately 350 mg per therapeutic intervention, approximately 80 mg to approximately 330 mg per therapeutic intervention, approximately 85 mg to approximately 300 mg per therapeutic intervention, approximately 90 mg to approximately 280 mg per therapeutic intervention, approximately 95 mg to approximately 250 mg per therapeutic intervention, approximately 100 mg to approximately 230 mg per therapeutic intervention, approximately 105 mg to approximately 200 mg per therapeutic intervention, approximately 110 mg to approximately 190 mg per therapeutic intervention, approximately 115 mg to approximately 175 mg per therapeutic intervention, approximately 120 mg to approximately 165 mg per therapeutic intervention, approximately 125 mg to approximately 160 mg per therapeutic intervention or approximately 130 mg to approximately 155 mg per therapeutic intervention. In some embodiments, 3-MMC is administered to the subject in an amount in a range of 20 mg to 500 mg, 22 mg to 490 mg, 27 mg to 470 mg, 30 mg to 450 mg, 33 mg to 435 mg, 40 mg to 410 mg, 47 mg to 390 mg, 50 mg to 375 mg, 55 mg to 360 mg, 57 mg to 350 mg, 60 mg to 320 mg, 63 mg to 300 mg, 67 mg to 290 mg, 70 mg to 270 mg, 75 mg to 260 mg, 77 mg to 250 mg, 80 mg to 240 mg, 85 mg to 220 mg, 90 mg to 210 mg or 100 mg to 200 mg per therapeutic intervention. It will be appreciated that each individual range of amount of 3-MMC administered represents a single, separate embodiment.

In some embodiments, 3-MMC is administered to the subject in an amount of 20, 25, 30, 35, 40, 45, 50, 55, 60, 65, 67, 70, 73, 75, 77, 80, 83, 85, 87, 90, 93, 95, 97, 100, 103, 107, 110, 113, 115, 117, 120, 123, 125, 127, 130, 133, 137, 140, 143, 145, 147, 150, 153, 155, 157, 160, 163, 167, 170, 173, 175, 177, 180, 183, 185, 187, 190, 193, 195, 197, 200, 220, 240, 250, 275, 290, 300, 310, 320, 330, 340, 350, 360, 370, 380, 390 or 400 mg per therapeutic intervention. In particular embodiments, 3-MMC is administered in an amount of 50 mg per therapeutic intervention, 100 mg per therapeutic intervention, 150 mg per therapeutic intervention, 200 mg per therapeutic intervention, 250 mg per therapeutic intervention, 300 mg per therapeutic intervention, 350 mg per therapeutic intervention or 400 mg per therapeutic intervention.

In some embodiments, 3-MMC is administered to the subject in a dosage calculated according to mass per body weight, e.g. mg 3-MMC per Kg body weight of the subject. In some embodiments, 3-MMC is administered to the subject in a dosage range of approximately 0.5 mg/Kg to approximately 7 mg/Kg body weight per therapeutic intervention, approximately 0.75 mg/Kg to approximately 6.5 mg/Kg body weight per therapeutic intervention, approximately 1.0 mg/Kg to approximately 6.0 mg/Kg body weight per therapeutic intervention, approximately 1.25 mg/Kg to approximately 5.5 mg/Kg body weight per therapeutic intervention, approximately 1.5 mg/Kg to approximately 5 mg/Kg body weight per therapeutic intervention, approximately 1.75 mg/Kg to approximately 4.5 mg/Kg body weight per therapeutic intervention, approximately 2.0 mg/Kg to approximately 4.25 mg/Kg body weight per therapeutic intervention, approximately 2.25 mg/Kg to approximately 4.0 mg/Kg body weight per therapeutic intervention, approximately 2.5 mg/Kg to approximately 3.75 mg/Kg body weight per therapeutic intervention, approximately 2.75 mg/Kg to approximately 3.5 mg/Kg body weight per therapeutic intervention body weight per therapeutic intervention. It will be appreciated that each individual range of 3-MMC per Kg body weight administered represents a single, separate embodiment.

In some embodiments, 3-MMC is administered to the subject in a dosage of 1.0, 1.25, 1.5, 1.75, 2.0, 2.25, 2.5, 2.75, 3.0, 3.25, 3.5, 3.75, 4.0, 4.25, 4.5, 4.75, 5.0 or 5.5 mg/Kg body weight per therapeutic intervention. In specific embodiments, 3-MMC is administered to the subject in a dosage of 1, 1.5, 2, 2.5 or 3 mg/Kg body weight per therapeutic intervention.

3-MMC can be administered to the subject via methods including, but not limited to oral administration, intravenous administration, insufflation (nasal administration), mucosal administration, rectal administration, transdermal administration and inhalation (e.g. dry powder or vapor inhalation). In specific embodiments of the method of the invention, the 3-MMC is administered to the subject via oral administration. In particular embodiments, 3-MMC is administered orally to the subject in an amount of 50 mg per therapeutic intervention, 100 mg per therapeutic intervention, 150 mg per therapeutic intervention, 200 mg per therapeutic intervention, 250 mg per therapeutic intervention, 300 mg per therapeutic intervention, 350 mg per therapeutic intervention or 400 mg per therapeutic intervention.

It will be appreciated that a psychotherapeutic intervention can be an individual, or isolated psychotherapeutic intervention, e.g. a therapy or counseling "session", or a part of a regimen of psychotherapeutic intervention, for example, a series of such psychotherapeutic intervention "sessions".

As used herein the phrase "treatment regimen" refers to a treatment plan that specifies the type of treatment, dosage, schedule and/or duration of a treatment provided to a subject in need thereof (e.g., a subject diagnosed with a pathology, condition or disorder). The selected treatment regimen can be an aggressive one which is expected to result in the best clinical outcome (e.g., complete cure of the pathology) or a more moderate one which may relief symptoms of the pathology yet results in incomplete cure of the pathology. It will be appreciated that in certain cases the more aggressive treatment regimen may be associated with some discomfort to the subject or adverse side effects (e.g., nausea, tachycardia). The dosage, schedule and duration of treatment can vary, depending on the severity of condition/disorder/pathology and the selected type of treatment, and those of skills in the art are capable of adjusting the type of treatment with the dosage, schedule and duration of treatment.

In some embodiments of the method of the invention, the 3-MMC is administered once during the psychotherapeutic intervention, or once per session, Ire other embodiments, the 3-MMC is administered more than once during the psychotherapeutic intervention, e.g. twice during the psychotherapeutic intervention or session, three times during the psychotherapeutic intervention or session, four times during the psychotherapeutic intervention or session or more than four times during the psychotherapeutic intervention or session.

In some embodiments, the psychotherapeutic intervention is effected prior to, concomitant with, or shortly after exposure to 3-MMC. The time interval between the psychotherapeutic intervention and administering the 3-MMC, or between administering the 3-MMC and the psychotherapeutic intervention can range from 1 hour to 48 hours, from 1 hour to 24 hours, from 1 hour to 18 hours, from 1 hour to 16 hours, from 1 hour to 12 hours, from 1 hour to 10 hours, from 1 hour to 8 hours, from 1 hour to 6 hours, from 1 hour to 4 hours and from 1 hour to 2 hours, 0.1 hours to 2 hours, from 0.25 hours to 1.5 hours and from 0.5 hours to 1.0 hours. The desired time interval can be determined according to, for example, the formulation of the 3-MMC, the condition to be treated, the treated subject.

Safety and pharmacokinetic studies with animal models (Shimshoni et al J Psychopharm, 2015; 29:734-43) have indicated that peak serum concentrations of 3-MMC are apparent within 5-10 minutes after oral administration, and that the apparent plasma half-life, after oral ingestion, is approximately 0.8 hours. The present inventors have observed that, in some embodiments the onset of human subject's perception of 3-MMC's effect is approximately 30-90 minutes following oral administration, varying according to whether the 3-MMC was administered to a fasting (more rapid onset), or following a meal (less rapid onset). In some cases, the perception of peak effect of 3-MMC in human subjects occurred between 10 to 30 minutes after the initial perception of onset of 3-MMC's effect. The present inventors further observed that the duration of perception of the effect of 3-MMC in human subjects was, in most cases, for no greater than 4 hours following oral administration.

Thus, in some embodiments, the 3-MMC is administered at least twice during the psychotherapeutic intervention or session. In some embodiments, the 3-MMC is administered twice during the psychotherapeutic intervention or session, at intervals of 1-8 hours between closings. In other embodiments, the 3-MMC is administered twice or three times during the psychotherapeutic intervention or session, at intervals of 2-7 hours between closings. In other embodiments, the 3-MMC is administered twice or three times during the psychotherapeutic intervention or session, at intervals of 3-6 hours between dosings. In other embodiments, the 3-MMC is administered twice or three times during the psychotherapeutic intervention or session, at intervals of 1-4 hours between dosings. In other embodiments, the 3-MMC is administered twice or three times during the psychotherapeutic intervention or session, at intervals of 1-3 hours between dosings. In yet other embodiments, the 3-MMC is administered twice or more during the psychotherapeutic intervention or session, at intervals of 1-2 hours between dosings.

In some embodiments, 3-MMC is administered in multiple doses (e.g. more than once) during the psychotherapeutic intervention or session, where each administration is of the same dosage of 3-MMC (e.g. 3×100 mg, 2×150 mg, 2×200 mg, and the like). In other embodiments, 3-MMC is administered in multiple doses (e.g. more than once) during a psychotherapeutic intervention or session, where each administration is of a different dosage of 3-MMC (e.g. 1×150 mg followed by 1×100 mg; 1×200 mg followed by 1×100 mg, followed by a third dose of 1×100 mg; 1×200 mg, followed by 1×150 mg, and the like). Combinations of initial higher and subsequent lower doses, as well as combinations of initial lower, and subsequent higher doses, as well as subsequent dosages alternating between lower and higher than the initial dose are also envisioned.

It will be appreciated that, in some embodiments, psychotherapeutic interventions comprising administration of 3-MMC, according to the methods of the present invention, can be consecutive interventions comprising administration of 3-MMC (e.g. sessions) within a regimen or treatment plan of psychotherapeutic interventions, and in other embodiments, interventions comprising administration of 3-MMC can be interspersed within a regimen or treatment plan which comprises psychotherapeutic interventions without administration of 3-MMC. In some embodiments in which interventions comprising administration of 3-MMC are interspersed within a regimen or treatment plan which comprises psychotherapeutic interventions without administration of 3-MMC, the psychotherapeutic interventions comprising administration of 3-MMC can be interspersed regularly between interventions without administration of 3-MMC throughout the regimen or treatment plan, or, in other embodiments, psychotherapeutic interventions comprising administration of 3-MMC can be included between with interventions without administration of 3-MMC in a non-regular manner, throughout the regimen or treatment plan. In one non-limiting example, a series of psychotherapeutic interventions (sessions) comprising administration of 3-MMC may be included for a limited period of time as an adjunct to a treatment plan or regimen predominantly including interventions without administration of 3-MMC. Such a regimen or treatment plan can be implemented, for example, in order to address a specific aspect of a subject's therapy especially suited for treatment with the psychotherapeutic interventions comprising 3-MMC of the present invention.

According to some embodiments, a regimen or treatment plan comprising psychotherapeutic interventions (sessions) of the method of the present invention comprising administration of 3-MMC can include psychotherapeutic interventions (sessions) of the method of the present invention at intervals of 2-4 hours, 4-6 hours, 6-12 hours, 12-18 hours, 1.8-24 hours, 36 hours, 48 hours, 3 days, 4 days, 5 days, 6 days, 1 week, 2 weeks, 3 weeks, 1 month, 2 months, 3 months or more. As detailed hereinabove, a regimen or treatment plan comprising psychotherapeutic interventions (sessions) of the method of the present invention comprising administration of 3-MMC can include psychotherapeutic interventions (sessions) of the method of the present invention at regular intervals during a regimen of treatment, or irregularly throughout a regimen.

As used herein, the subject is a mammalian subject, and preferably a human subject. Psychotherapeutic interventions are often directed to modifying an outcome, and/or helping a person change and/or overcome problems in desired ways. In some embodiments, subject is suffering from distress, and the psychotherapeutic intervention of the method of the present invention is for distress of the subject. In specific embodiments, the treating the subject with the method of the present invention is for reducing distress of the subject suffering from distress.

As used herein, the term "distress" refers to reaction to a "stressor", and constituting an underlying component of anxiety and depression. Distress can lead to a disorder that results in altered or abnormal behavior, function, or subjective distress in one or more of the following intrapersonal or interpersonal realms: mood, anxiety, memory, cognition, consciousness, perception, sexual experience, sleep, substance use/addiction, personality, attention/concentration, psychosis, identity, eating, or bodily function or integrity.

In some embodiments, the subject is suffering from distress selected from the group consisting of cognitive distress, emotional distress, behavioral distress, relationship distress and spiritual distress.

As used herein, cognitive distress refers to distress which results from problematic and/or inaccurate thinking processes, for example, someone who justifies abusive behavior, and takes no responsibility and offers the rationalization that the other person is to blame.

As used herein, emotional distress refers to distress which is related to feelings. Examples are problematic anger, fear, or grief.

As used herein, behavioral distress refers to distress that is observable to others as it is manifested in a person's behavior, for example, aggression to others or self-harm by self-mutilation.

As used herein, relationship distress refers to distress which results from conflict in a relationship. One non-limiting example is of couple in the process of a conflictual divorce.

As used herein, spiritual distress refers to distress related to the larger issue(s) of meaning and purpose to life. One non-limiting example is an individual who attempts suicide and then has a spiritual revelation that they need to reach out to others who are suicidal.

Typically, a subject suffering from distress experiences social, interpersonal, and/or occupational impairment or dysfunction. The cause (etiology, or stressor) may be idiopathic (unknown), or it may be due to a recognized psychosocial stressor, a medical disorder, or a neurological disorder. It should be appreciated that any type distress can be compatible with aspects of the invention.

3-MMC-assisted psychotherapeutic intervention according to the method of the present invention can be suitable for a wide range of disorders and conditions which are indicated for psychotherapeutic intervention. Many such diagnostic categories are listed in the American Psychiatric Society's Diagnostic and Statistical Manual, Fifth Edition (DSM-V, 2013) and in the World Health Organization's International Statistical Classification of Diseases and Related Health Problems, $10^{th}$ Revision (ICD 10), in particular, Chapter V of the ICD 10: "Mental and Behavioral Disorders". Thus, according to some embodiments of the invention, the subject is diagnosed with a condition or disorder selected from the group consisting of the disorders and conditions in following Table I:

TABLE I

| Disorder, Condition or Problem -Designation | Disorder, Condition or Problem DSM-V | Disorder, Condition or Problem ICD-10 |
|---|---|---|
| Acute stress disorder | 308.3 | F43.0 |
| Adjustment disorder | | |
| Adjustment disorder, Unspecified | 309.9 | F43.20 |
| Adjustment disorder, With anxiety | 309.24 | F43.22 |
| Adjustment disorder, With depressed mood | 309.0 | F43.21 |
| Adjustment disorder, With disturbance of conduct | 309.3 | F43.24 |
| Adjustment disorder, With mixed anxiety and depressed mood | 309.28 | F43.23 |
| Adjustment disorder, With mixed disturbance of emotions and conduct | 309.4 | F43.25 |
| Adult physical abuse by nonspouse or nonpartner, Confirmed | | |
| Adult sexual abuse by nonspouse or nonpartner, Confirmed | | |
| Agoraphobia | 300.22 | F40.00 |
| Amphetamine-type substance use disorder | | |
| Anorexia nervosa | 307.1 | |
| Anorexia nervosa, Binge-eating/purging type | | F50.02 |
| Anorexia nervosa, Restricting type | | F50.01 |
| Antisocial personality disorder | 301.7 | F60.2 |
| Anxiety disorder due to another medical condition | 293.84 | F06.4 |
| Attention-deficit/hyperactivity disorder | | |
| Avoidant personality disorder | 301.82 | F60.6 |
| Avoidant/restrictive food intake disorder | 307.59 | F50.8 |
| Binge-eating disorder | 307.51 | F50.8 |
| Body dysmorphic disorder | 300.7 | F45.22 |
| Child sexual abuse, Suspected or Confirmed | | |
| Cocaine use disorder | | |
| Cocaine use disorder-Mild | 305.60 | F14.10 |
| Cocaine use disorder-Moderate | 304.20 | F14.20 |
| Cocaine use disorder-Severe | 304.2 | F14.20 |
| Conduct disorder | | |
| Dependent personality disorder | 301.6 | F60.7 |
| Depressive disorder due to another medical condition | 293.83 | |
| Depressive disorder due to another medical condition, With depressive features | | F06.31 |
| Depressive disorder due to another medical condition, With major depressive-like episode | | F06.32 |
| Depressive disorder due to another medical condition, With mixed features | | F06.34 |
| Discord with neighbor, lodger, or landlord | V60.89 | Z64.4 |
| Disruption of family by separation or divorce | V61.03 | Z63.5 |
| Female orgasmic disorder | 302.73 | F52.31 |
| Female sexual interest/arousal disorder | 302.72 | F52.22 |
| Gambling disorder | 312.31 | F63.0 |
| Generalized anxiety disorder | 300.02 | F41.1 |
| High expressed emotion level within family | V61.8 | Z63.8 |
| Hoarding disorder | 300.3 | F42 |
| Illness anxiety disorder | 300.7 | F45.21 |
| Kleptomania | 312.32 | F63.2 |
| Major depressive disorder, Recurrent episode | | |
| Male hypoactive sexual desire disorder | 302.71 | F52.0 |
| Narcissistic personality disorder | 301.81 | F60.81 |
| Obsessive-compulsive disorder | 300.3 | F42 |
| Obsessive-compulsive personality disorder | 301.4 | F60.5 |
| Overweight or obesity | | |
| Other circumstances related to adult abuse by nonspouse or nonpartner | | |
| Other circumstances related to spouse or partner neglect | | |
| Other circumstances related to spouse or partner violence, physical or sexual | | |

TABLE I-continued

| Disorder, Condition or Problem -Designation | Disorder, Condition or Problem DSM-V | Disorder, Condition or Problem ICD-10 |
|---|---|---|
| Other circumstances related to spouse or partner abuse, Psychological | | |
| Other circumstances related to child neglect | | |
| Other circumstances related to child psychological abuse | | |
| Other circumstances related to child sexual abuse | | |
| Other specified sexual dysfunction | | |
| Other specified personality disorder | 301.89 | F60.89 |
| Other specified anxiety disorder | 300.09 | F41.8 |
| Other specified feeding or eating disorder | 307.59 | F50.8 |
| Other specified gender dysphoria | 302.6 | F64.8 |
| Other specified trauma- and stressor-related disorder | 309.89 | F43.8 |
| Other (or unknown) substance use disorder | | |
| Other or unspecified stimulant use disorder | | |
| Other personal history of psychological trauma | V15.49 | Z65.8 |
| Opioid use disorder | | |
| Oppositional-defiant disorder | 313.81 | F91.3 |
| Parent-child relational problem | V61.20 | Z62.820 |
| Personal history (past history) of neglect in childhood | V15.42 | Z62.812 |
| Personal history (past history) of physical abuse in childhood | V15.41 | Z62.810 |
| Personal history (past history) of psychological abuse in childhood | V15.42 | Z62.811 |
| Personal history (past history) of sexual abuse in childhood | V15.41 | Z62.810 |
| Personal history (past history) of spouse or partner neglect | V15.42 | Z91.412 |
| Personal history (past history) of spouse or partner psychological abuse | V15.42 | Z91.411 |
| Personal history (past history) of spouse or partner violence, physical | V15.41 | Z91.410 |
| Personal history (past history) of spouse or partner violence, sexual | V15.41 | Z91.410 |
| Personal history of self-harm | V15.59 | Z91.5 |
| Phase of life problem | V62.89 | Z60.0 |
| Posttraumatic stress disorder | 309.81 | F43.10 |
| Reactive attachment disorder | 313.89 | F94.3 |
| Relationship distress with spouse or intimate partner | V61.10 | Z63 |
| Religious or spiritual problem | V62.89 | Z65.8 |
| Sedative, hypnotic, or anxiolytic use disorder | | |
| Separation anxiety disorder | 309.21 | F93.0 |
| Sex counseling | V65.49 | Z70.9 |
| Sibling relational problem | V61.8 | Z62.891 |
| Social anxiety disorder (social phobia) | 300.23 | F40.10 |
| Social exclusion or rejection | V62.4 | Z60.4 |
| Spouse or partner abuse, Psychological, Confirmed | | |
| Stimulant use disorder | | |
| Tobacco use disorder | | |
| Uncomplicated bereavement | | |
| Unspecified anxiety disorder | 300.00 | F41.9 |
| Unspecified alcohol-related disorder | 291.9 | F10.99 |
| Unspecified caffeine-related disorder | 292.9 | F15.99 |
| Unspecified cannabis-related disorder | 292.9 | F12.99 |
| Unspecified cocaine-related disorder | | F14.99 |
| Unspecified communication disorder | 307.9 | F80.9 |
| Unspecified gender dysphoria | 302.6 | F64.9 |
| Unspecified personality disorder | 301.9 | F60.9 |
| Unspecified problem related to social environment | V62.9 | Z65.9 |
| Unspecified depressive disorder | 311 | F32.9 |
| Unspecified tobacco-related disorder | 292.9 | F17.209 |
| Victim of crime, terrorism or torture | V62.82 | Z65.4 |

In specific embodiments, the subject is diagnosed with a condition or disorder selected from the group consisting of personal history of psychological trauma, parent-child relational problem, personal history (past history) of neglect in childhood, personal history (past history) of physical abuse in childhood, personal history (past history) of psychological abuse in childhood, personal history (past history) of sexual abuse in childhood, personal history (past history) of spouse or partner neglect, personal history (past history) of spouse or partner psychological abuse, personal history (past history) of spouse or partner physical violence, personal history (past history) of spouse or partner sexual violence, phase of life problem, relationship distress with spouse or intimate partner, stimulant use disorder and posttraumatic stress disorder.

In specific embodiments, the subject is diagnosed with relationship distress with spouse or intimate partner, religious or spiritual problem, stimulant use disorder, posttraumatic stress disorder or tobacco use disorder.

In some embodiments, the subject is diagnosed with a stress-sensitive disorder. As used herein, a "stress-sensitive disorder" refers to any condition, disease or disorder that results, at least in part, from exposure to stress or is exacerbated, at least in part, from exposure to stress. Non-limiting examples of stress-sensitive disorders include Post-traumatic Stress Disorder (PTSD), Bipolar Disorder, Acute Stress Disorder, anxiety disorders such as Generalized Anxiety Disorder, Obsessive-Compulsive Disorder, social anxiety disorders, Panic Disorders, phobias, obsessive compulsive disorders, and Trichotillomania. It should be appreciated that any stress-sensitive disorder can be compatible with aspects of the invention.

It will be appreciated that, in some embodiments, the subject may be diagnosed with more than a single condition or disorder. In the event of multiple diagnoses for a subject's condition, psychotherapeutic interventions and/or the methods of treating of the present invention may be directed to treatment of a single diagnosis among the multiple diagnoses, according to priorities determined by the therapist and/or subject, or, in some embodiments, it may be suitable to treat more than a single condition or disorder among the subject's diagnoses concomitantly, rather than sequentially. For example, and just by way of illustration, in a subject diagnosed with both substance addiction and depression, the therapist's treatment regimen may choose to include use of the method(s) of the invention for treatment of the depression before proceeding to treatment of the substance addiction, or the therapist may choose to include use of the method(s) of the invention in treatment of some of the multiple diagnoses of the subject, and use other therapeutic modalities in addressing the subject's multiple diagnoses.

Administering 3-MMC to a subject undergoing psychotherapeutic intervention according to the methods of the present invention can be useful in reducing distress in a subject in need thereof. In some embodiments, reducing the distress comprises identifying and changing thought and/or behavior patterns in said subject.

Typically, the goal of psychotherapeutic intervention is to help the subject change and overcome problems in desired ways. One of the outcomes of effective psychotherapeutic intervention is a reduction in the number and/or frequency of interventions required for particular conditions/diagnoses. Further non-limiting outcomes of effective psychotherapeutic intervention include, but are not limited to greater stability in the work/home environment, improved behaviors, improved employment functioning, improved vocational functioning, reduction of cognitive stress, reduction of emotional stress, improved living situation, improved family relationships, improved social relationships, improved sense of meaning to life, improved sense of purpose to life, reduction of mental health symptoms, reduction of addiction behaviors, reduction in chemical dependencies and the like.

Thus, in some embodiments, where the subject is being treated with method of the present invention for reducing distress, reducing distress in the subject comprises reducing the number and/or frequency of psychotherapeutic interventions. In other embodiments, reducing distress in the subject comprises improving stability in the work/home environment, improving behaviors, improving employment functioning, improving vocational functioning, reducing cognitive stress, reducing emotional stress, improving the subject's living situation, improving the subject's family relationships, improving social relationships, improving the subject's sense of meaning to life, improving the subject's sense of purpose to life, reducing mental health symptoms, reducing addiction behaviors and reducing chemical dependencies. In specific embodiments, reducing distress in the subject comprises one or more of reducing chemical dependencies, greater vocational or academic functioning and improved family and/or social relationships.

Methods and instruments for diagnosing, evaluating the severity of and monitoring the progress of therapy of a subject's psychological or psychiatric disorder or condition being treated with psychotherapeutic intervention are well known in the art.

A non-limiting list of suitable instruments for diagnosing, monitoring and evaluating subjects' progress prior to, during or following therapy using the methods of the present invention is provided in Table II:

TABLE II

MONITORING AND OUTCOME MEASURES

| Objective | Measure | Link/Info |
|---|---|---|
| Safety | Adverse Events | |
| | Serious Adverse Events | |
| | Monitor Session Rating Form | Griffiths et al., 2006 |
| | Challenging Experience Questionnaire | Used in Josh Woolley UCSF protocol and by the Johns Hopkins Group.<br>The Challenging Experience Questionnaire: Characterization of challenging experiences with psilocybin mushrooms.<br>Barrett et al, J Psychopharmacol 2016; 12: 1279-9 |
| Feasibility | Rate of patient recruitment | |
| | Rate of patient retention | |
| | Client Satisfaction Questionnaire 8 | Larsen et al 1979 Evaluation and Program Planning 2: 197-207 |
| | Qualitative: Patient Experience | British Columbia Centre on Substance Abuse |
| Efficacy - Decreased substance use | Timeline Follow-back (NIDA) | Robinson et al 2014 Psych Addict Behav 28: 154-62 |
| | Urine Drug Screen | |
| | Urinary Cotinine Test (tobacco) | |
| | Carbon Monoxide Breath Test (tobacco) | |

TABLE II-continued

| MONITORING AND OUTCOME MEASURES | | |
|---|---|---|
| Objective | Measure | Link/Info |
| | Hair/Nail Analysis (Alcohol) | |
| | DSM-5 Substance Use Disorder Diagnostic Checklist | bup practice node/19556 |
| | Addiction Severity Index-Lite (ASI-Lite) | m.breining |
| | Severity of Dependence Scale | Adapted from Gossop et al 1995 Addiction 90: 607-614 |
| | Structured Clinical Interview for DSM-5 Research Version (SCID-5-RV)- Module E: Substance Use Disorders | See Am Psychiatric Assoc website |
| | Short Inventory of Problems - Alcohol and Drugs | Example found is alcohol only version, but Alcohol and Drug version does exist. See CASAA in University of New Mexico .edu website |
| Efficacy - Enhanced motivation to reduce or stop substance use | Thoughts About Abstinence Questionnaire | Hall S M, Havassy B E, Wasserman D A. Commitment to abstinence and acute stress in relapse to alcohol, opiates, and nicotine. J Consult Clin Psychol. 1990; 58: 175-181. The four-item TAA was used to assess motivation to quit and abstinence self-efficacy. TAA motivation to quit scores have been shown to predict smoking cessation treatment outcome, and TAA abstinence self-efficacy scores have been shown to mediate the effect of extended cognitive behavioral therapy on treatment outcome |
| | Substance Use Recovery Evaluator | See Kings College (UK) website- Scales, Measures and Instruments |
| | Self Efficacy Scales | See University of Maryland, Baltimore County website Self-Efficacy Scales |
| | Readiness To Change Questionnaire (Treatment Version) RCQ-TV | Treatment Improvement Protocol (TIP) Series, No. 35. Center for Substance Abuse Treatment. Rockville (MD): Substance Abuse and Mental Health Services Administration (US); 1999. |
| | Recovery Progression Measure | Initial Development and Psychometric Properties of a New Measure of Substance Use Disorder "Recovery Progression": The Recovery Progression Measure (RPM) Elison S, Davies G, Ward J. *Subst Use Misuse*. 2016 Jul. 28; 51(9): 1195-206 |
| | Drug-Taking Confidence Questionnaire | Annis, H. M., Sklar, S. M. & Turner, N. E. (1997). The Drug-Taking Confidence Questionnaire (DTCQ): User's Guide. Toronto, Canada: Addiction Research Foundation, Centre for Addiction and Mental Health. Annis, H. M. & Martin, G. (1985). Drug-Taking Confidence Questionnaire. Toronto, Canada: Addiction Research Foundation. |
| | The Stages of Change Readiness and Treatment Eagerness Scale (SOCRATES 8A) | CASAA in University of New Mexico .edu website |
| | Alcohol Abstinence Self-Efficacy Scale | DiClemente, C. C., Carbonari, J. P., Montgomery, R. P. G. & Hughes, S. O. (1994). The Alcohol Abstinence Self-Efficacy Scale. Journal of Studies on Alcohol, 55, 141-148. |
| Mechanism - Evaluate whether or not characteristics of the psilocybin administration session experiences (e.g. Intensity) mediate effects of psilocybin on short-term persisting effects and post-session substance use behaviour | Mystical Experience Questionnaire | R R Griffiths, R. R., W A Richards, W. A., U McCann, U., & R Jesse, R., (2006), "Psilocybin can occasion mystical-type experiences having substantial and sustained personal meaning and spiritual significance". Psychopharmacology, 187(3), 268-83; commentaries on pp. 284-292. |
| | Altered State of Consciousness Questionnaire (5D-ASC) | Dittrich, A, Lamparter, D, Maurer, M. Zurich, Switzerland: PSIN PLUS; 2006. 5D-ABZ: Fragebogen zur Erfassung Aussergewöhnlicher Bewusstseinszustände. Eine kurze Einführung [5D-ASC: Questionnaire for the assessment of altered states of consciousness. A short introduction]. |
| | Persisting Effects Questionnaire | Griffiths, R. R., Richards, W. A., McCann, U., & Jesse, R. (2006), "Psilocybin can occasion mystical-type experiences having substantial and sustained personal meaning and spiritual significance." Psychopharmacology, 187(3), 268-83, commentaries on pp. 284-292. |

TABLE II-continued

| MONITORING AND OUTCOME MEASURES | | |
|---|---|---|
| Objective | Measure | Link/Info |
| | States of Consciousness Questionnaire | Griffiths, R. R., Richards, W. A., McCann, U., & Jesse, R. (2006), "Psilocybin can occasion mystical-type experiences having substantial and sustained personal meaning and spiritual significance." Psychopharmacology, 187(3), 268-83, commentaries on pp. 284-292. |
| | Hallucinogen Rating Scale | Could not locate sample online. Used in Bogenschutz protocol and by Griffiths et al 2006. |
| | Mysticism Scale | See Northern Virginia Community College website: Laura Shulman |
| | APZ | Used in Hendricks protocol and by Griffiths et al 2006. Based on article below, the 5D-ASC could be an updated version. Psychometric Evaluation of the Altered States of Consciousness Rating Scale (OAV) Erich Studerus,* Alex Gamma, and Franz X. Vollenweider PLoS One. 2010: 5(8): e12412. |
| | The Addiction Research Center Inventory (ARCI), 49-item version | Could not find example online. Used by Bogenschutz et al 2015 and by Griffiths et al 2006 |
| | Visual Effects Questionnaire | Used by Johnson et al 2014. |
| Neurobio Mechanism | fMRI Craving Task Pre- & Post-experimental session | What other fMRI tasks might be useful to shed light on potential mechanisms & lasting effects of psilocybin on neural activity? Stress response, Response to emotional stimuli, Inhibitory control tasks? Task-free fMRI assessing resting state functional connectivity? |
| Efficacy - Mediators of treatment | | |
| Motivation | Thoughts About Abstinence Questionnaire | see above |
| | Substance Use Recovery Evaluator | see above |
| | Readiness To Change Questionnaire (Treatment Version) RCQ-TV | see above |
| | Readiness Ruler | See ADULT MEDUCATION website Assessment Tools |
| Self-efficacy | Self Efficacy Scales | see above |
| | Drug-Taking Confidence Questionnaire | see above |
| Craving | Brief Substance Craving Scale | Somoza, E., Dyrenforth, S., Goldsmith, J., Mezinskis, J., & Cohen, M., 1995. In search of a universal drug craving scale. Paper presented at the Annual Meeting of the American Psychiatric Association, Miami Florida. See Univ of Washington website: ADAI |
| | Alcohol Craving Visual Analog Scale (ACVAS) | |
| | Short Inventory of Problems (SIP) Scale | Miller et al, National Institute on Alcohol Abuse and Alcoholism Project MATCH Monograph Series Volume 4 Pages 49, 51 |
| Depression | PROMIS Emotional Distress - Depression (used by VIDUS) | 2008 PROMIS Health Organization and PROMIS Cooperative Group |
| | Centre for Epidemiologic Studies Depression Scale | National Institutes of Mental Health, US |
| | Beck's Depression Inventory | |
| | Hamilton Depression Rating Scale | |
| | Quick Inventory of Depressive Symptomology | Rush et al, Biol Psychiatry (2003) 54: 573-83. |
| Anxiety | PROMIS Emotional Distress - Anxiety (used by VIDUS) | PROMIS Item Bank v1.0 - Emotional Distress - Anxiety - Short Form 8a |
| | State-Trait Anxiety Inventory | Speilberger et al. Mind Garden Redwood CA |
| | Beck's Anxiety Inventory | Beck, A. T., Epstein, N., Brown, G., Steer, R. A. (1988). An inventory for measuring clinical anxiety: Psychometric properties. Journal of Consulting and Clinical Psychology, 56, 893-897. |

TABLE II-continued

| MONITORING AND OUTCOME MEASURES | | |
|---|---|---|
| Objective | Measure | Link/Info |
| | Hamilton Anxiety Rating Scale | Hamilton M. The assessment of anxiety states by rating. Br J Med Psychol 1959; 32: 50-55. |
| Mood | Profile of Mood States Questionnaire | Top End Sports and McNair et al. (1971) Manual for the Profile of Mood States. San Diego, CA: Educational and Industrial Testing Service. Grove, J. R., & Prapavessis, H. (1992). Preliminary evidence for the reliability and validity of an abbreviated Profile of Mood States. International Journal of Sport Psychology, 23, 93-109. |
| Self-Compassion | Self-Compassion Scale (Short Form) | 2011, Raes et al, Clin Psych Psychother 18 250-255 |
| Spiritual Dimensions | Persisting Effects Questionnaire | See above (also has items on depression & anxiety) |
| | Spirituality Index of Well Being | Daaleman, T. P. & Frey, B. B. (2004). The Spirituality Index of Well-Being: A new instrument for health-related quality of life research. Annals of Family Medicine, 2, 499-503. |
| | Strength of Religious Faith Questionnaire | Used in Hendricks protocol. |
| | Meaning in Life Questionnaire | Steger, M. F., Frazier, P., Oishi, S., & Kaler, M. (2006). The Meaning in Life Questionnaire: Assessing the presence of and search for meaning in life. Journal of Counseling Psychology, 53, 80-93. |
| | Satisfaction with Life Scale | Diener, E., Emmons, R. A., Larsen, R. J., & Griffin, S. (1985). The Satisfaction with Life Scale. Journal of Personality Assessment, 49, 71-75 |
| | ASPIRES Spiritual Transcendence Scale | See Bogenschutz protocol, by Bogenschutz et al 2015, and by Griffiths et al 2006. |
| | Brief Multidimensional Measure of Religiousness/Spirituality | See: Fetzer Institute, National Institute on Aging Working Group: Multidimensional Measurement of Religiousness, Spirituality for Use in Health Research. A Report of a National Working Group. Supported by the Fetzer Institute in Collaboration with the National Institute on Aging. Kalamazoo, MI: Fetzer Institute, 2003 (1999) and Research on Aging: "Measuring Multiple Dimensions of Religion and Spirituality for Health Research," Ellen L. Idler, Marc A. Musick, Christopher G. Ellison, Linda K. George, Neal Krause, Marcia G. Ory, Kenneth I. Pargament, Lynda H. Powell, Lynn G. Underwood, David R. Williams, 2003, 25: 4. |

In specific embodiments subjects' progress prior to, during or following therapy using the methods of the present invention is evaluated using at least one of the Beck Depression Inventory, the Beck Anxiety Inventory, the Beck Hopelessness Scale, for PTSD: UCLA PTSD Index for DSM IV, GAD-7, The Primary Care PTSD Screen and others, the Oxford Happiness Inventory and Addictions assessments selected from Table 2.

It will be appreciated that the method of the present invention can be combined with other therapeutic modalities, in addition to the psychotherapeutic intervention. Pharmacotherapy is a common adjunct to psychotherapeutic intervention in modern treatment plans, for achieving both short term and long-term results in the subject undergoing psychotherapeutic intervention. Thus, in some embodiments, the subject is being treated with at least one drug selected from the group consisting of selective serotonin re-uptake inhibitors (SSRIs), mono-amine-oxidase (MAO) inhibitors, serotonin-dopamine antagonists, analgesics, anti-hypertensive drugs, anti-allergenics, anti-inflammatory drugs, poison antidotes, anti-convulsive drugs, anti-infective drugs, muscle relaxants and local anesthetics. In specific embodiments, the method of the present invention further comprises administering to the subject at least one drug selected from abovementioned group.

Yet further, non-pharmacological adjuncts to psychotherapy have become popular recently, and can also be integrated within the psychotherapeutic intervention of the methods of the present invention. In addition, the context of the psychotherapy is important and attention needs to be paid to both the set (ie expectations of the client/patient/subject) and the setting or environment of the experience (eg music, art, decorations, food, videos, etc.). Thus, in some embodiments, the method of the present invention further comprises exposing the subject to an adjunct therapeutic, non-pharmacological modality selected from the group consisting of, for example, at least one of music, food, choice of space for therapy, visual stimulus, audio stimulus, thermal comfort, art, books, interior design, objects that have an impact (e.g. spiritual cards), presence (or absence) of other individuals, therapist mannerisms, furnishings suitable for therapy sessions.

The 3-MMC of some embodiments of the invention can be administered to a subject per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the 3-MMC accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, PA, latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of some embodiments of the invention may also be formulated in rectal compositions such as suppositories or retention enemas, using, e.g., conventional suppository bases such as cocoa butter or other glycerides.

Pharmaceutical compositions suitable for use in context of some embodiments of the invention include compositions wherein the active ingredients are contained in an amount effective to achieve the intended purpose. More specifically, a therapeutically effective amount means an amount of 3-MMC effective, when combined with psychotherapeutic intervention, to treat, prevent, alleviate or ameliorate symptoms of a disorder or condition in the subject.

Determination of a therapeutically effective amount is well within the capability of those skilled in the art, especially in light of the detailed disclosure provided herein.

For any preparation used in the methods of the invention, the therapeutically effective amount or dose can be estimated initially from animal models. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p.1).

Dosage amount and interval may be adjusted individually to provide levels of 3-MMC sufficient to induce or suppress the biological effect (minimal effective concentration, MEC). The MEC will vary for each preparation, but can be estimated from animal models. Dosages necessary to achieve the MEC will depend on individual characteristics and route of administration. Detection assays can be used to determine plasma concentrations.

As detailed hereinabove, depending on the severity and responsiveness of the condition to be treated, dosing can be of a single or a plurality of administrations, with course of treatment lasting from several days to several weeks or until cure is effected or diminution of the disorder or condition is achieved.

The amount of a composition to be administered will, of course, be dependent on the subject being treated, the severity of the affliction, the manner of administration, the judgment of the prescribing physician, etc.

Compositions of some embodiments of the invention may, if desired, be presented in a pack or dispenser device, such as an FDA approved kit, which may contain one or more unit dosage forms containing 3-MMC as the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

Thus, according to some embodiments, there is provided a kit for use in treating a subject undergoing a psychotherapeutic intervention comprising a therapeutically effective amount of 3-methylmethcathinone (3-MMC) and instructions for the use of 3-MMC in conjunction with said psychotherapeutic intervention. Types of psychotherapeutic interventions suitable for combination with administering 3-MMC according to the methods of the present invention are described in detail hereinabove. In some embodiments, the instructions indicate that the psychotherapeutic intervention is for distress in the subject. In other embodiments, the psychotherapeutic intervention is selected from the group consisting of psychoanalytic and psychodynamic therapy, behavioral therapy, cognitive therapy, humanistic therapy and integrative or holistic therapy.

It is expected that during the life of a patent maturing from this application many relevant methods for treating subjects undergoing psychotherapeutic intervention with 3-MMC will be developed and the scope of the term "administering 3-MMC to a subject undergoing a psychotherapeutic intervention" is intended to include all such new technologies a priori.

As used herein the term "about" or "approximately" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion. Generally, the nomenclature used herein and the clinical procedures utilized in the present invention include psychiatric, psychotherapeutic, psychological, psychoanalytical, counseling, pharmacological and pharmaceutical techniques. Such techniques are thoroughly explained in the literature. See, for example, the DSM-V and the ICD 10, both of which are incorporated by reference as if fully set forth herein. Other general references are provided throughout this document. The procedures therein are believed to be well known in the art and are provided for the convenience of the reader. All the information contained therein is incorporated herein by reference.

The following case studies exemplify some aspects of some embodiments of the methods of the present invention for treating subjects undergoing psychotherapeutic intervention by administering 3-MMC.

Case Study I: Post-Traumatic Stress Disorder (PTSD)

Male age 41 suffering from PTSD who was previously incorrectly diagnosed with bipolar disorder, unable to work was under the care of a psychiatrist with no improvement in 4 years. After three 3-MMC-assisted psychotherapy sessions this individual was no longer diagnosable with either PTSD or bipolar and was able to return to gainful employment. In this case, the therapy consisted of both a male and female therapist in a room designed for this therapy (soft lighting, bed, attractive pillows, carefully chosen music, inspirational art—spiritual and nature). The patient was taught relaxation and breathing techniques and briefed in what to expect from the experience. In this case 200 milligrams of 3-MMC was given orally and the patient then lay down on the bed and listened to soothing music for 1.5 hours with eye shades on (internal experience). Then the patient sat up, took off the eye shades and engaged the therapists in an exploration of the historical event which resulted in PTSD. The therapists engaged in psychotherapy for 2 hours after which the patient once again lay down and put on the eyeshades for another 2 hours. Subsequently, the patient re-engaged with the therapists and explored his insights about how he could reframe the traumatic memory to be a positive learning experience.

Case Study II: Couples Therapy

Heterosexual couple married for 17 years were caught in a cycle of repetitive conflict over what they both agreed were trivial issues. They described intense, mutual emotional reactivity and angry outbursts which was problematic enough to begin to discuss divorcing. As a last attempt to resolve their conflicts they agreed to participate in once a month 3-MMC couple's therapy. Over a 6-month period (6 sessions) they were both able to take responsibility for their own problematic behaviour and negotiate a more functional relationship. In this case the therapy consisted of one female therapist who assessed the couple and prepared for the 3-MMC sessions with 2 non-3MMC sessions where the couple was taught a specific communication technique (Non Violent Communication). The space was a normal therapist's office with comfortable furnishings, 3 chairs and an adjoining kitchen. The 3-MMC was given orally which a dosage of 150 milligrams each followed by a booster dosage of 100 milligrams given 1 hour after the first dosage. The couple alternated between periods of listening to relaxing music and conversation, where they explored their own perspectives on how to communicate in relationship both currently and historically. The counsellor would translate some of the couple's statements in the language of non-violent communication and encourage self responsibility. The end of the session occurred 5 hours after the booster dose and a light meal was prepared and served and the couple and therapist ate and debriefed the session. The couple met with the therapist twice between each of the 3-MMC sessions for traditional couples counseling. Their current relationship is not conflict free but they are no longer discussing divorce.

Case Study III: Relationship Distress

Female 40-year-old single professional woman entered in to 3-MMC assisted therapy to understand why her relationships with men never lasted more than a few months. After four 3-MMC assisted psychotherapy sessions she understood her previously unconscious behaviour pattern which related to her family of origin. In this case the patient was assessed and prepared by the female therapist in two preliminary sessions where the patients relationship history was explored. The patient was encouraged to consider the connection between her experience of her parent's relationship when she was a child and her reaction to men she dated which was coloured by her past history. The location of the therapy was the living room of the therapist which had been prepared with inspirational art and wall hangings. The sound system consisted of headphones and an ipod with soothing/spiritual music. On the treatment days the patient was given 300 milligrams of 3-MMC orally. The treatment session started by the therapist guiding a meditation exercise and then the patient was encouraged to reflect internally by lying down with eyeshades and listening to the music. In this case the internal experience was 20 minutes after which the patient removed the eyeshades and turned off the music and proceeded to express intense emotions which related to her past anger at her mother. The therapist acknowledged the importance of this emotional expression which continued for 2.5 hours after which the patient resumed the lying position and the therapist held her hand in silence for 1 hour. The session ended with the patient exploring the insights she gained from the experience. Two subsequent non-3MMC therapy sessions solidified the integration of the experience.

While she is still single the few dates she has been on have been a more positive experience then had occurred historically.

Case Study IV: Post-Traumatic Stress Disorder (PTSD) and Generalized Anxiety Disorder (GAD)

A 30 year old female had been suffering from Post traumatic Stress Disorder (PTSD), depression, and General Anxiety Disorder (GAD).

The symptoms she experienced were panic attacks, hyperventilation, pain in the chest, numbness, and tingling in the extremities, Irritable-Bowel Syndrome (IBS), nightmares, and insomnia.

The PTSD had been caused by a particular life-threatening event, as well as other related incidences that had unfolded in her youth. The psychological ramifications of these events went undiagnosed for many years, although she was eventually treated for anxiety and depression. She refused however, to take the anti-depressants that her physician was willing to prescribe her, and only occasionally would take 5-10 mg Oxazepam for acute panic attacks.

At the time that she started with the 3-MMC-assisted psychotherapy, she had been suffering from an occupational burnout for 4 months already cf. DC-10 Z-73.0.

3-MMC was administered twice weekly on two consecutive days at a dosage of 200-400 mg each time for a period of 8 weeks. Starting at week 5; 3-MMC-assisted psychotherapy took place once a week. Each session lasted 6.5-10 h with an average of 8.5 h per session. The neural correlates that 3-MMC procured upon her during these sessions allowed her to recall the traumatic experiences at the root of her PTSD with the therapist, without the usual associated paralyzing fear, in a putative 5-HT1A-agonist dependent manner. Subsequent reconsolidation of these memories in the aftermath of the transient neural endogenous pharmacokinetic profile induced by 3-MMC, led the level of associated fear to decrease with each subsequent session.

At week 5 during the 3-MMC-assisted psychotherapy regimen, she then started Eye Movement Desensitization and Reprogramming (EMDR) therapy once week for 1 h, two days prior to 3-MMC-assisted psychotherapy. 40 mg of propanolol was administered 1 h prior to each EMDR session in order to extinguish the remaining fear-associated memories.

Taken together, the results of these case studies indicate that administration of 3-MMC to subjects undergoing psychotherapeutic intervention for diverse conditions and disorders, including couples counseling, treatment of PTSD and GAD and relationship distress, can be an effective adjunct to a variety of psychotherapeutic interventions.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of augmenting psychotherapeutic intervention comprising administering 3-methylmethcathinone (3-MMC) to a subject undergoing said psychotherapeutic intervention.

2. The method of claim 1, wherein said 3-MMC is administered prior to said psychotherapeutic intervention.

3. The method of claim 1, wherein said 3-MMC is administered during said psychotherapeutic intervention.

4. The method of claim 3, wherein said 3-MMC is administered at least twice during said psychotherapeutic intervention.

5. The method of claim 1, wherein said 3-MMC is administered after said psychotherapeutic intervention.

6. The method of claim 1, wherein said 3-MMC is administered to said subject in an amount of approximately 50 mg to approximately 500 mg per therapeutic intervention.

7. The method of claim 6, wherein said 3-MMC is administered to said subject in an amount of approximately 100 mg to approximately 400 mg per therapeutic intervention.

8. The method of claim 6, wherein said 3-MMC is administered to said subject in an amount of approximately 100 mg to approximately 200 mg per therapeutic intervention.

9. The method of claim 1, wherein said 3-MMC is administered to said subject in an amount of approximately 100 mg or 200 mg per therapeutic intervention.

10. The method of claim 1, wherein said psychotherapeutic intervention is for distress of said subject.

11. The method of claim 10, wherein said treating is for reducing said distress in said subject.

12. The method of claim 10, wherein said distress is selected from the group consisting of cognitive, emotional, behavioral, relationship and spiritual distress.

13. The method of claim 10, wherein said distress is a condition or disorder selected from the group consisting of personal history of psychological trauma, parent-child relational problem, personal history (past history) of neglect in childhood, personal history (past history) of physical abuse in childhood, personal history (past history) of psychological abuse in childhood, personal history (past history) of sexual abuse in childhood, personal history (past history) of spouse or partner neglect, personal history (past history) of spouse or partner psychological abuse, personal history (past history) of spouse or partner physical violence, personal history (past history) of spouse or partner sexual violence, phase of life problem, relationship distress with spouse or intimate partner, stimulant use disorder and posttraumatic stress disorder.

14. The method of claim 10, wherein said subject is diagnosed with a stress-sensitive disorder selected from the group consisting of Post-traumatic Stress Disorder (PTSD), Bipolar Disorder, Acute Stress Disorder, anxiety disorders such as Generalized Anxiety Disorder, Obsessive-Compulsive Disorder, social anxiety disorders, Panic Disorders, phobias, obsessive compulsive disorders, and Trichotillomania.

15. The method of claim 1, wherein said psychotherapeutic intervention is selected from the group consisting of psychoanalytic and psychodynamic therapy, behavioral therapy, cognitive therapy, humanistic therapy and integrative or holistic therapy.

16. The method of claim 15, wherein said psychotherapeutic intervention is humanistic therapy or integrative/holistic therapy.

17. The method of claim 10, wherein reducing said distress comprises at least one of the following: improving stability in the work/home environment, improving behaviors, improving employment functioning, improving vocational functioning, reducing cognitive stress, reducing emotional stress, improving the subject's living situation, improving the subject's family relationships, improving social relationships, improving the subject's sense of meaning to life, improving the subject's sense of purpose to life, reducing mental health symptoms, reducing addiction behaviors and reducing chemical dependencies.

18. The method of claim 10, wherein reducing said distress comprises reducing the number and/or frequency of psychotherapeutic interventions, and/or reducing addiction behaviors and reducing chemical dependencies.

* * * * *